United States Patent [19]

Manimaran et al.

[11] Patent Number: 5,315,027
[45] Date of Patent: May 24, 1994

[54] CATALYTIC PROCESS FOR PREPARING THE ALKYL ESTERS OF IBUPROFEN

[75] Inventors: Thanikavelu Manimaran; Tse-Chong Wu; Felix M. Orihuela, all of Baton Rouge, La.

[73] Assignee: Ethyl Corporation, Richmond, Va.

[21] Appl. No.: 62,906

[22] Filed: May 11, 1993

[51] Int. Cl.$^5$ ............................................. C07C 69/76
[52] U.S. Cl. .................................... 560/105; 562/406
[58] Field of Search ................. 560/105, 406; 562/406

[56] References Cited

U.S. PATENT DOCUMENTS 4,990,658  2/1991  Stahly et al. .................... 562/406

Primary Examiner—Paul J. Killos
Attorney, Agent, or Firm—Richard J. Hammond

[57] ABSTRACT

A process for preparing alkyl esters of ibuprofen is provided. A 1-halo-1-(4-isobutylphenyl)ethane is reacted in an anhydrous medium with carbon monoxide in the presence of an alkoxide source at a temperature between about 10° C. and about 200° C. An excess of several moles of alcohol is preferred. An acid such as hydrogen chloride may also be added. As catalyst, a palladium compound having at least one acid-stable ligand is present; however, an excess of ligand over palladium is advantageous.

42 Claims, No Drawings

CATALYTIC PROCESS FOR PREPARING THE ALKYL ESTERS OF IBUPROFEN

TECHNICAL FIELD

This invention relates to a process for preparing the alkyl esters of ibuprofen and the free carboxylic acid thereof.

BACKGROUND OF THE INVENTION

Among the processes known for preparing 2-(4-isobutylphenyl)propionic acid or esters thereof is that of Shimizu et al. (U.S. Pat. No. 4,694,100, issued September, 1987), who teach the reaction of p-isobutyl-styrene with carbon monoxide and water or alcohol in the presence of a palladium catalyst and a mineral acid, e.g., HCl. This patent also teaches the alternative reaction of p-isobutylstyrene with carbon monoxide and hydrogen in the presence of a metal complex carbonyl catalyst to produce 2-(4-isobutylphenyl)propionaldehyde, which is then oxidized to produce the desired product. The preparation of the starting material for this reaction is disclosed as the reaction of isobutylbenzene with acetaldehyde in the presence of sulfuric acid, producing 1,1-bis(4-isobutylphenyl)ethane, which is then catalytically cracked to produce p-isobutylstyrene and isobutylbenzene.

Another process for preparing ibuprofen is that of European Patent Application 284,310 (Hoechst Celanese, published September, 1988), which teaches that ibuprofen can be prepared by carbonylating 1-(4-isobutylphenyl)ethanol with carbon monoxide in an acidic aqueous medium and in the presence of a palladium compound/phosphine complex and dissociated hydrogen and halide ions, which are preferably derived from a hydrogen halide. This process has the disadvantage of starting with 1-(4-isobutylphenyl)ethanol, a compound which is not economical to make by known processes.

Gardano et al. (U.S. Pat. No. 4,536,595, issued August, 1985) teach the preparation of alkaline salts of certain alphaarylpropionic acids by reaction with carbon monoxide, at substantially ambient temperature and pressure conditions, of the corresponding arylethyl secondary halide in an anhydrous alcoholic solvent in the presence of alkaline hydroxides and, as catalyst, a salt of cobalt hydrocarbonyl.

Alper et al. in *J. Chem. Soc. Chem. Comm.*, 1983, 1270–1271, discloses that alkenes can react with carbon monoxide, water, hydrochloric acid and a mixture of palladium and copper to produce the hydrocarboxylated product, branched chain carboxylic acid. Oxygen is necessary to succeed in the reaction. Subsequently, Alper et al. have disclosed similar catalyst systems, but employing a chiral ligand as being successful in asymmetric hydrocarboxylation reactions. See Alper et al., PCT Application, WO 91 03,452 and *J. Am. Chem. Soc.*, 112, 2803–2804 (1990).

Japanese Kokiku Patent No. SHO (1981)-35659 discloses an anhydrous method of producing a 2-(4-isobutylphenyl) propion acid ester by treating 2-(4-isobutyl-phenyl) ethanol with carbon monoxide in a solution of an alkanol and a catalyst such as palladium/-bis(triphenylphosphine)dichloro complex. The solution may also contain up to ten percent (10%) of a mineral acid, such as hydrogen chloride.

THE INVENTION

In the following specification, "alkyl" means straight or branched chain alkyl having 1 to 20 carbon atoms and includes, for example, methyl, ethyl, propyl, isopropyl, butyl, isobutyl, secondary butyl, tertiary butyl, pentyl, isopentyl, neopentyl, hexyl, heptyl, octyl, 2-ethylhexyl, 1,1,3,3-tetramethylbutyl, nonyl, decyl, dodecyl, tetradecyl, hexadecyl, octadecyl and eicosyl, and the like; and "halo" (also "halogen") means fluoro, chloro, bromo or iodo.

In accordance with the present invention, an ibuprofen alkyl ester is prepared by carbonylating a 1-halo-1-(4-isobutylphenyl)ethane with carbon monoxide in an anhydrous acidic or neutral medium containing at least 1 mol of a source of alkoxide ions per mol of halocarbon compound at a temperature of between about 25° C. and about 200° C. a and carbon monoxide pressure of at least about one atmosphere in the presence of palladium metal or a palladium compound in which the palladium has a valence of 1 or 2 and at least one acid-stable ligand.

The present invention embraces any salts, racemates and individual optical isomers thereof of the compounds of the following formula (I) having a chiral carbon atom.

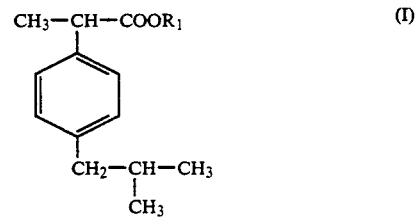

where $R_1$ is alkyl.

The 1-halo-1-(4-isobutylphenyl)ethane which is carbonylated in the practice of this invention may be 1-chloro-1-(4-isobutylphenyl)ethane or 1-bromo-1-(4-isobutylphenyl)ethane, and it may be synthesized by any known technique.

The carbonylation of 1-halo-1-(4-isobutylphenyl)ethane is conducted at a temperature between about 10° C. and about 200° C., preferably about 50°–150° C., and most preferably about 90°–135° C. Higher temperatures can also be used. It has been found that a small advantage in yield is obtained by gradually increasing the temperature within the preferred ranges during the course of the reaction.

The partial pressure of carbon monoxide in the reaction vessel is at least about 1 atmosphere at ambient temperature (or the temperature at which the vessel is charged). Any higher pressures of carbon monoxide can be used up to the pressure limits of the reaction apparatus. A pressure up to about 4500 psig (about 31 MPa) is convenient in the process. More preferred is a pressure from about 300 to about 3000 psig (about 2 to about 21 MPa) at the reaction temperature, and most preferred is a pressure from about 800 to about 2000 psig (about 5 to about 14 MPa).

The carbonylation is conducted in the presence of at least about one mol of a source of alkoxide ions per mol of 1-halo-1-(4-isobutylphenyl)ethane. Controlling the amount of alkoxide source used in the process of this invention is advantageous in terms of producing the highest yields. Therefore, an amount from about 2 to about 50 mols of alkoxide source per mol of 1-halo-1-(4-isobutylphenyl)ethane is preferred, and an amount from about 2 to about 24 mols of alkoxide source per mol of the halocarbon compound is most preferred. The product of the reaction is an alkyl ester of ibuprofen.

By "source of alkoxide ions", as used herein, is intended to mean a compound (or mixture of compounds) that is present in the reaction solution [the mixture of the halo compound, catalyst, ligand and solvent (if any)] and produces in such reaction solution the alkoxide anion, i.e., the ion $R_1O^-$ where $R_1$ is as previously defined. The source of such alkoxide ions is from a compound selected from the group consisting of $RC(OR_1)_3$, $(R_2)C(OR_1)_2$, $Ti(OR_1)_4$, $Al(OR_1)_3$, $B(OR_1)_3$, $HC(O)OR_1$ $P(O)(R_1)_3$ and $P(OR_1)_3$ where R is hydrogen or individually the or same or different than $R_1$ and $R_1$ is as previously defined. Examples of compounds that will produce alkoxide ions in the reaction solution used in the process of this invention are: trimethyl orthoformate; triethyl orthoformate; triethyl borate; trimethyl borate; trimethyl phosphate; ethyl formate; methyl formate; methyl phosphite; ethyl phosphite; ethyl phosphate; aluminum ethoxide; titanium-(IV) propoxide; and titanium(IV) methoxide.

In a preferred embodiment of this invention, the carbonylation reaction is initiated under neutral conditions, i.e., with no added acid. It can also be performed in the presence of an added acid. When acids are added, such acids include sulfuric acid, phosphoric acid, or sulfonic acids. Aprotic acids, notably Lewis acids, e.g., aluminum chloride, boron trifluoride, titanium tetrachloride, zinc chloride, etc., can also be used in the process of this invention. A hydrogen halide such as hydrogen chloride or hydrogen bromide is preferred. The hydrogen halide is added as a gas phase or as a liquid phase (in the form of a solution with the halo compound as the solvent, if any). Any concentration may be used. Hydrogen chloride is particularly preferred, at a solution concentration of up to about 10%; more highly preferred is a solution concentration from about 10% to about 30%. The amount of acid added is such as to provide up to about 40 mols of hydrogen ion per mol of 1-halo-1-(4-isobutylphenyl)ethane; more preferred is an amount to provide up to about 10 mols of hydrogen ion per mol of 1-halo-1-(4-isobutylphenyl)ethane; the most preferred amount provides up to about 4 mols of hydrogen ion per mol of 1-halo-1-(4-isobutylphenyl)ethane. It should be noted, however, that the entire system must be anhydrous to effect improved yields of the ibuprofen ester. Hence, drying of the solvent/reactant is important for the process of the present invention.

The carbonylation process of this invention is conducted in the presence of a reaction-promoting quantity of a) a palladium metal or palladium compound in which the palladium has a valence of 1 or 2 and b) at least one acid-stable ligand. Ligands which may be used include monodentate or multidentate electron-donating substances such as those containing elements P, N, O and the like, and those containing multiple bonds such as olefinic compounds. Examples of such acid-stable ligands are trihydrocarbylphosphines, including trialkyl- and triarylphosphines, such as tri-n-butyl-, tricyclohexyl-, and triphenylphosphine; lower alkyl and aryl nitriles, such as benzonitrile and n-propionitrile; ligands containing pi-electrons, such as an allyl compound or 1,5-cyclooctadiene; piperidine, piperazine, trichlorostannate(II), and acetylacetonate; and the like. In one embodiment, the palladium or palladium compound and ligand are added as a pre-formed complex of palladium, such as bis(triphenylphosphine)palladium(II) chloride or bromide, tetrakis(triphenylphosphine)palladium-(0), or any other similar complex.

In a preferred embodiment, active catalytic species are formed in situ by the addition to the reaction mixture of the individual components, i.e., a ligand and a palladium compound such as palladium(II) chloride, bromide, nitrate, sulfate, or acetate. In the most preferred embodiment, triphenylphosphine and palladium-(II) chloride are used and are added individually or together, either simultaneously or sequentially.

The amount of palladium (as the metal or the compound) preferably employed is such as to provide from about 4 to about 8000 mols of 1-halo-1-(4-iso-butylphenyl)ethane per mol of palladium; more preferred is an amount to provide from about 100 to about 4000 mols of 1-halo-1-(4-isobutylphenyl)ethane per mol of palladium; the most preferred amounts provide from about 200 to 2000 mols of 1-halo-1-(4-iso-butylphenyl)ethane per mol of palladium. The process of this invention is conducted in the presence of at least one mol of ligand per mol of palladium. More preferably about 2 to about 40 mols of ligand per mol of palladium are present, and most preferably about 4 to about 20 mols of ligand per mol of palladium are used. Even more highly preferred is an amount from about 8 to about 12 mols of ligand per mol of palladium.

The presence of a solvent is not required in the process of this invention since excess anhydrous halo compound may provide any effects desired from a solvent. However, a solvent may be desirable in some circumstances. Those solvents which can be used include one or more of the following: ketones, for example, acetone, methyl ethyl ketone, diethyl ketone, methyl-n-propyl ketone, acetophenone, and the like; linear, poly and cyclic ethers, for example, diethyl ether, di-n-propyl ether, di-n-butyl ether, ethyl-n-propyl ether, glyme (the dimethyl ether of ethylene glycol), diglyme (the dimethyl ether of diethylene glycol), tetrahydrofuran, dioxane, 1,3-dioxolane, and similar compounds; and aromatic hydrocarbons, for example, toluene, ethyl benzene, alkyl-substituted benzenes (isobutylbenzene), xylenes, and similar compounds. Acids and esters may also be used, such as formic or acetic acid or ethyl acetate, etc. When an ester is used as solvent, the product is the corresponding ester of ibuprofen or a mixture of the esters if mixtures of acids (or esters) are used. Most highly preferred are ketones, especially acetone and methyl ethyl ketone. When solvents are used, the amount can be up to about 10 mL per gram of 1-halo-1-(4-isobutylphenyl)ethane, but the process is most advantageously conducted in the presence of about 1 to 10 mL per gram of 1-halo-1-(4-isobutylphenyl)ethane.

The ester of ibuprofen formed in the process of the present invention is converted to the acid (to free ibuprofen) by conventional methods of hydrolysis.

The following examples are given to illustrate the process of this invention and are not intended as a limitation thereof.

EXAMPLE 1

A 100 mL Hastelloy B autoclave was charged with a mixture of CEBB (500 mg; 2.54 mmol), $PdCl_2$ (20 mg; 0.11 mmol), $Ph_3P$ (100 mg; 0.38 mmol), anhydrous $AlCl_3$ (50 mg; 0.38 mmol) and triethylorthoformate (1.0 g; 6.7 mmol) in 35 mL of MEK. The mixture was carbonylated at 100° C. under 800 psi of CO for 50 hours to produce ibuprofen ethyl ester in 80% yield.

EXAMPLE 2

A 100 mL Hastelloy B autoclave was charged with a mixture of MEK (35 mL), CEBB (500 mg; 2.54 mmol), $PdCl_2$ (20 mg; 0.11 mmol), $Ph_3P$ (100 mg; 0.38 mmol), anhydrous $AlCl_3$ (100 mg; 0.76 mmol) and triethylborate (860 mg; 5.9 mmol). The mixture was carbonylated at 100° C. under 800 psi of CO for 16 hours. Product composition by GC analysis was: 44% CEBB, 48% ibuprofen ethyl ester.

EXAMPLES 3–4

Examples 3 and 4 were carried out in the same manner as Examples 1 and 2.

| Exp. | Catalyst | Alkoxide Ion | Pressure | Temp. | Time | Solvent | Yield |
|---|---|---|---|---|---|---|---|
| 3 | $PdCl_2/Ph_3P$ | $Ti(OPr)_4$ | 700 psig | 105° C. | 64 hours | MEK | 62% |
| 4 | $Pd(PPh_3)_2Cl_2$ | $NaOCH_3/HCO_2Me$ | 1 atm | 40° C. | 24 hours | $CH_2Cl_2$ | 17% |

We claim:
1. A process for preparing an alkyl ester of ibuprofen which comprises carbonylating a 1-halo-1-(4-isobutylphenyl)ethane with carbon monoxide in a neutral or acidic anhydrous medium containing at least about 1 mol of a source of alkoxide ions selected from the group consisting of $RC(OR_1)_3$, $(R)_2C(OR_1)_2$, $Ti(OR_1)_4$, $Al(OR_1)_3$, $B(OR_1)_3$, $HC(O)OR_1$, $P(O)(R_1)_3$ and $P(OR_1)$ where R is hydrogen or individually the same or different than $R_1$ and $R_1$ is alkyl per mol of 1-halo-1-(4-isobutylphenyl)ethane at a temperature between about 10° C. and about 200° C. and a carbon monoxide pressure of at least about one atmosphere in the presence of (a) a palladium metal or palladium compound in which the palladium has a valence of 1 or 2 and (b) at least one acid-stable ligand.
2. A process of claim 1 wherein the 1-halo-1-(4-isobutylphenyl)ethane is 1-chloro-1-(4-isobutylphenyl)ethane.
3. A process of claim 1 wherein the 1-halo-1-(4-isobutylphenyl)ethane is 1-bromo-1-(4-isobutylphenyl)ethane.
4. A process of claim 1 wherein the palladium compound is a palladium(II) compound.
5. A process of claim 4 wherein the palladium compound is palladium(II) chloride.
6. A process of claim 4 wherein the palladium compound is palladium(II) bromide.
7. A process of claim 1 wherein the ligand is a monodentate phosphine ligand.
8. A process of claim 1 wherein the ligand is a tri(hydrocarbyl)phosphine.
9. A process of claim 8 wherein the ligand is triphenylphosphine.
10. A process of claim 1 wherein the palladium compound is bis(triphenylphosphine)palladium(II) chloride or bromide.
11. A process of claim 1 wherein the amount of palladium compound employed is such as to provide about 4–8000 mols of 1-halo-1-(4-isobutylphenyl)ethane per mol of palladium.
12. A process of claim 1 wherein the palladium compound and ligand are employed in amounts such as to provide about 4–20 mols of ligand per mol of palladium in the reaction mixture.
13. A process of claim 1 wherein the palladium compound and ligand are employed in amounts such as to provide about 8–12 mols of ligand per mol of palladium in the reaction mixture.
14. A process of claim 1 wherein the carbonylation is conducted in the presence of triethyl orthoformate and no added acid.
15. A process of claim 1 wherein the carbonylation is conducted in the presence of from about 2 to about 50 mols of said source of alkoxide ions per mol of 1-halo-1-(4-isobutylphenyl)ethane.
16. A process of claim 1 wherein the carbonylation is conducted in the presence of from about 1 to about 24 mols of said alkoxide ions per mol of 1-halo-1-(4-isobutylphenyl)ethane.
17. A process of claim 1 wherein the carbonylation is conducted in the presence of from about 2 to about 24 mols of alkoxide ions per mol of 1-halo-1-(4-iso-butylphenyl)ethane.
18. A process of claim 1 wherein the carbonylation is conducted in the presence of added hydrogen halide.
19. A process of claim 18 wherein the hydrogen halide is hydrogen chloride.
20. A process of claim 18 wherein the hydrogen halide is hydrogen bromide.
21. A process of claim 18 wherein the hydrogen halide is added to an anhydrous solution containing a trialkyl orthoformate.
22. A process of claim 21 wherein the hydrogen halide is hydrogen chloride and the concentration of the solution is a up to about 30% (by weight) hydrogen chloride.
23. A process of claim 21 wherein the hydrogen halide is hydrogen chloride and the concentration of the solution is a up to about 10% (by weight) hydrogen chloride.
24. A process of claim 19 wherein the amount of hydrogen halide added is an amount up to about 40 mols per mol of 1-halo-1-(4-isobutylphenyl)ethane.
25. A process of claim 1 wherein the carbonylation is conducted in the presence of a Lewis acid.
26. A process of claim 25 wherein the Lewis Acid is aluminum chloride.
27. A process of claim 1 wherein the carbonylation is conducted in a solvent.
28. A process of claim 27 wherein the solvent is a ketone.
29. A process of claim 28 wherein the solvent is acetone.
30. A process of claim 28 wherein the solvent is methyl ethyl ketone.
31. A process of claim 1 wherein the temperature is in the range of about 50°–100° C.
32. A process of claim 1 wherein the temperature is in the range of about 90°–135° C.
33. A process of claim 32 wherein the temperature is gradually increased during the reaction.
34. A process of claim 1 wherein the carbon monoxide pressure is in the range of about 300–3000 psig.
35. A process of claim 1 wherein the carbon monoxide pressure is in the range of about 800–2000 psig.

36. A process for preparing the methyl ester of ibuprofen which comprises carbonylating 1-chloro-1-(4-isobutylphenyl)ethane with carbon monoxide in an anhydrous, acidic medium containing methyl ethyl ketone as a solvent and about 8-24 mols of anhydrous trimethyl orthoformate per mol of said 1-chloro-1-(4-isobutylphenyl)ethane at a temperature in the range of about 50°-150° C. and a carbon monoxide pressure in the range of about 800-1000 psig in the presence of (a) a palladium(II) compound and (b) at least one acid-stable monodentate phosphine ligand and in the presence of an amount of hydrogen chloride such as to provide an amount up to about 10 mols of hydrogen chloride per mol of 1-chloro-1-(4-isobutylphenyl)ethane.

37. A process of claim 36 wherein the palladium(II) compound is palladium(II) chloride and the ligand is triphenylphosphine.

38. A process of claim 36 wherein the palladium and the ligand are present in amounts such as to provide about 200-2000 mols of said 1-chloro-1-(4-isobutylphenyl)ethane per mol of the mixture of palladium and about 2-20 mols of ligand per mol of the palladium.

39. A process of claim 36 wherein the hydrogen chloride is added as an anhydrous solution in methylethylketone with a concentration from about 10% (by weight) to about 30% (by weight) HCl.

40. A process for preparing the methyl ester of ibuprofen which comprises carbonylating 1-chloro-1-(4-isobutylphenyl)ethane with carbon monoxide in an anhydrous, neutral or acidic medium containing methyl ethyl ketone as a solvent and about 8-24 mols of trimethyl orthoformate per mol of said 1-chloro-1-(4-isobutylphenyl)ethane and no added acid at a temperature in the range of about 50°-150° C. and a carbon monoxide pressure in the range of about 800-2000 psig (about 5-14 MPa), in the presence of (a) a palladium(II) compound and (b) at least one acid-stable monodentate phosphine ligand.

41. A process of claim 40 wherein the palladium(II) compound is palladium(II) chloride and the ligand is triphenylphosphine.

42. A process of claim 40 wherein the palladium and the ligand are present in amounts such as to provide about 200-2000 mols of said 1-chloro-1-(4-isobutylphenyl)ethane per mol of palladium and about 4-20 mols of ligand per mol of palladium.

* * * * *